(12) United States Patent
Crosby et al.

(10) Patent No.: US 9,079,019 B2
(45) Date of Patent: Jul. 14, 2015

(54) APPARATUS AND METHODS FOR ANCHORING ELECTRODE LEADS FOR USE WITH IMPLANTABLE NEUROMUSCULAR ELECTRICAL STIMULATOR

(75) Inventors: Peter Andrew Crosby, Blaine, MN (US); Choll Kim, San Diego, CA (US); Jason Alan Shiroff, Edina, MN (US); Prashant Brijmohansingh Rawat, Blaine, MN (US); Dan Sachs, Minneapolis, MN (US)

(73) Assignee: Mainstay Medical Limited, Swords, County Dublin (IE)

( * ) Notice: Subject to any disclaimer, the term of this patent is extended or adjusted under 35 U.S.C. 154(b) by 0 days.

(21) Appl. No.: 13/564,584

(22) Filed: Aug. 1, 2012

(65) Prior Publication Data
US 2013/0131766 A1    May 23, 2013

Related U.S. Application Data

(60) Provisional application No. 61/514,327, filed on Aug. 2, 2011.

(51) Int. Cl.
*A61N 1/05* (2006.01)
*A61B 17/04* (2006.01)
*A61B 17/86* (2006.01)

(52) U.S. Cl.
CPC .......... *A61N 1/0558* (2013.01); *A61B 17/0401* (2013.01); *A61B 2017/0403* (2013.01); *A61B 2017/045* (2013.01); *A61B 2017/0427* (2013.01);

(Continued)

(58) Field of Classification Search
CPC ................. A61N 1/0558; A61N 1/05–1/0597; A61B 17/0401–17/0466
See application file for complete search history.

(56) References Cited

U.S. PATENT DOCUMENTS

| 3,077,884 A | 2/1963 | Batrow et al. |
| 3,893,463 A | 7/1975 | Williams |

(Continued)

FOREIGN PATENT DOCUMENTS

| CN | 1211930 C | 7/2005 |
| WO | WO 2006/133445 A2 | 12/2006 |

(Continued)

OTHER PUBLICATIONS

Wikipedia, "Interference Fit," http://en.wikipedia.org/wiki/Interference_fit, accessed Dec. 4, 2014.*
Garmirian, et al., Discriminating Neurogenic from Myopathic Disease via Measurement of Muscle Anisotrophy, Muscle Nerve, 39(1):16-24 (2009) (Abstract only).

(Continued)

*Primary Examiner* — Michael Kahelin
(74) *Attorney, Agent, or Firm* — Foley & Lardner LLP; Christopher C. Bolten; Nicola A. Pisano

(57) ABSTRACT

Apparatus and methods for tethering an electrode lead to an anatomical structure within a patient using a coupling member are provided. An anchor configured to be secured to the anatomical structure and an electrode lead suitable for neuromuscular stimulation of spinal muscles and/or nerves innervating one or more muscles that contribute to spine stability may be used. The electrode lead is configured to be coupled to the anchor via the coupling member by securing a first end of the coupling member to the electrode lead and securing a second end of the coupling member to an eyelet of the anchor to place the electrode lead at a desired anatomical site within the patient.

11 Claims, 7 Drawing Sheets

(52) U.S. Cl.
CPC . *A61B 2017/0451* (2013.01); *A61B 2017/0456* (2013.01); *A61B 2017/8655* (2013.01)

(56) References Cited

U.S. PATENT DOCUMENTS

| | | | |
|---|---|---|---|
| 4,026,301 A | 5/1977 | Friedman et al. | |
| 4,342,317 A | 8/1982 | Axelgaard | |
| 4,408,609 A | 10/1983 | Axelgaard | |
| 4,549,556 A * | 10/1985 | Tarjan et al. | 607/117 |
| 4,658,835 A | 4/1987 | Pohndorf | |
| 4,917,093 A | 4/1990 | Dufresne et al. | |
| 5,215,088 A | 6/1993 | Normann et al. | |
| 5,496,345 A | 3/1996 | Kieturakis et al. | |
| 5,501,452 A | 3/1996 | Halvorson | |
| 5,522,854 A | 6/1996 | Ideker et al. | |
| 5,733,307 A | 3/1998 | Dinsdale | |
| 5,741,321 A | 4/1998 | Brennen | |
| 5,916,172 A | 6/1999 | Hodges et al. | |
| 5,957,968 A | 9/1999 | Belden et al. | |
| 6,104,957 A | 8/2000 | Alo et al. | |
| 6,314,325 B1 | 11/2001 | Fitz | |
| 6,319,241 B1 | 11/2001 | King et al. | |
| 6,366,819 B1 | 4/2002 | Stokes | |
| 6,406,421 B1 | 6/2002 | Grandjean et al. | |
| 6,473,654 B1 * | 10/2002 | Chinn | 607/126 |
| 6,516,227 B1 | 2/2003 | Meadows et al. | |
| 6,527,787 B1 | 3/2003 | Fogarty et al. | |
| 6,600,956 B2 | 7/2003 | Maschino et al. | |
| 6,671,557 B1 | 12/2003 | Gliner | |
| 6,735,474 B1 | 5/2004 | Loeb et al. | |
| 6,839,594 B2 | 1/2005 | Cohen et al. | |
| 6,862,479 B1 | 3/2005 | Whitehurst et al. | |
| 7,096,070 B1 | 8/2006 | Jenkins et al. | |
| 7,206,641 B2 | 4/2007 | Ignagni et al. | |
| 7,239,918 B2 | 7/2007 | Strother et al. | |
| 7,286,879 B2 | 10/2007 | Wallace | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,337,005 B2 | 2/2008 | Kim et al. | |
| 7,337,006 B2 | 2/2008 | Kim et al. | |
| 7,444,181 B2 | 10/2008 | Shi et al. | |
| 7,447,546 B2 | 11/2008 | Kim et al. | |
| 7,450,993 B2 | 11/2008 | Kim et al. | |
| 7,489,561 B2 | 2/2009 | Armstrong et al. | |
| 7,493,175 B2 | 2/2009 | Cates et al. | |
| 7,502,651 B2 | 3/2009 | Kim et al. | |
| 7,580,753 B2 | 8/2009 | Kim et al. | |
| 7,668,598 B2 | 2/2010 | Herregraven et al. | |
| 7,684,866 B2 | 3/2010 | Fowler et al. | |
| 7,708,763 B2 | 5/2010 | Selover et al. | |
| 7,797,053 B2 | 9/2010 | Atkinson et al. | |
| 7,908,015 B2 | 3/2011 | Lazeroms et al. | |
| 7,917,230 B2 | 3/2011 | Bly | |
| 7,930,039 B2 | 4/2011 | Olson | |
| 8,082,039 B2 | 12/2011 | Kim et al. | |
| 8,170,690 B2 | 5/2012 | Morgan et al. | |
| 8,229,565 B2 | 7/2012 | Kim et al. | |
| 8,229,656 B2 | 7/2012 | Ikushima et al. | |
| 8,249,701 B2 | 8/2012 | Imran et al. | |
| 8,380,318 B2 | 2/2013 | Kishawi et al. | |
| 8,428,728 B2 | 4/2013 | Sachs | |
| 8,606,358 B2 | 12/2013 | Sachs | |
| 2001/0053885 A1 | 12/2001 | Gielen et al. | |
| 2002/0156513 A1 | 10/2002 | Borkan | |
| 2004/0111118 A1 | 6/2004 | Hill et al. | |
| 2004/0122482 A1 | 6/2004 | Tung et al. | |
| 2004/0236383 A1 | 11/2004 | Yelizarov | |
| 2005/0080472 A1 * | 4/2005 | Atkinson et al. | 607/126 |
| 2005/0154389 A1 | 7/2005 | Selover et al. | |
| 2006/0009827 A1 | 1/2006 | Kurth et al. | |
| 2006/0106416 A1 | 5/2006 | Raymond et al. | |
| 2006/0111746 A1 | 5/2006 | Foreman et al. | |
| 2006/0111754 A1 | 5/2006 | Rezai et al. | |
| 2006/0184222 A1 * | 8/2006 | Camps et al. | 607/129 |
| 2006/0235484 A1 | 10/2006 | Jaax et al. | |
| 2006/0241716 A1 | 10/2006 | Finch et al. | |
| 2007/0027501 A1 | 2/2007 | Jensen et al. | |
| 2007/0073357 A1 | 3/2007 | Rooney et al. | |
| 2007/0100377 A1 | 5/2007 | Armstrong et al. | |
| 2007/0100391 A1 | 5/2007 | Armstrong | |
| 2007/0100408 A1 | 5/2007 | Gerber | |
| 2007/0100411 A1 | 5/2007 | Bonde | |
| 2007/0135768 A1 | 6/2007 | Carlsen | |
| 2008/0103573 A1 | 5/2008 | Gerber | |
| 2008/0103579 A1 | 5/2008 | Gerber | |
| 2008/0132961 A1 | 6/2008 | Jaax et al. | |
| 2008/0167698 A1 | 7/2008 | Kim et al. | |
| 2008/0183221 A1 | 7/2008 | Burdulis | |
| 2008/0183257 A1 | 7/2008 | Imran et al. | |
| 2008/0228241 A1 | 9/2008 | Sachs | |
| 2008/0234791 A1 | 9/2008 | Arle et al. | |
| 2009/0112263 A1 | 4/2009 | Pool et al. | |
| 2009/0210041 A1 | 8/2009 | Kim et al. | |
| 2009/0259280 A1 | 10/2009 | Wilkin et al. | |
| 2010/0030227 A1 | 2/2010 | Kast et al. | |
| 2010/0036454 A1 | 2/2010 | Bennett et al. | |
| 2010/0082086 A1 | 4/2010 | Zhu | |
| 2010/0174240 A1 | 7/2010 | Wells et al. | |
| 2011/0022123 A1 | 1/2011 | Stancer et al. | |
| 2011/0224665 A1 | 9/2011 | Crosby et al. | |
| 2011/0224682 A1 | 9/2011 | Westlund et al. | |
| 2012/0035953 A1 | 2/2012 | Armstrong | |
| 2012/0116477 A1 | 5/2012 | Crowe et al. | |
| 2012/0283800 A1 | 11/2012 | Perryman et al. | |
| 2013/0023974 A1 * | 1/2013 | Amrani | 607/117 |
| 2013/0131766 A1 | 5/2013 | Crosby et al. | |
| 2013/0211487 A1 | 8/2013 | Fang et al. | |
| 2013/0245715 A1 | 9/2013 | Peterson | |
| 2013/0261696 A1 | 10/2013 | Thacker et al. | |
| 2013/0296966 A1 | 11/2013 | Wongsarnpigoon et al. | |
| 2013/0338730 A1 | 12/2013 | Shiroff et al. | |
| 2014/0046398 A1 | 2/2014 | Sachs et al. | |
| 2014/0058476 A1 | 2/2014 | Crosby et al. | |

FOREIGN PATENT DOCUMENTS

| | | |
|---|---|---|
| WO | WO-2007/051146 A1 | 5/2007 |
| WO | WO-2008/048471 A2 | 4/2008 |
| WO | WO 2009/134475 A1 | 11/2009 |

OTHER PUBLICATIONS

Hodges, et al., Intervetebral Stiffness of the Spine is Increased by Evoked Contraction of Transversus Abdominis and the Diaphragm: In Vivo Porcine Studies, Spine 28(23):2594-2601 (2003) (Abstract only).
Hodges, Is There a Role for Transversus Abdominis in Lumbo-Pelvis Stability? Manual Therapy, 4(2):74-86 (1999).
Holm, et al., Sensorimotor Control of the Spine, J. Electromyogr. Kinesiol. 12(3):219-34 (2002) (Abstract only).
Keller, et al., Muscular Contributions to Dynamic Dorsoventral Lumber Spine Stiffness, Eur. Spine J., 16(2):245-54 (2006).
Miyatani, et al., Validity of Estimating Limb Muscle Volume by Bioelectrical Impedance, J. Appl. Physiol., 91:386-394 (2001).
PCT International Search Report and Written Opinion dated Sep. 3, 2013 in related PCT Application No. PCT/US2013/045223.
PCT Written Opinion dated Aug. 23, 2013 in related PCT Application No. PCT/US2010/049148.
Rutkove, Electrical Impedance Myography: Background, Current State, and Future Directions, Muscle Nerve,40(6):936-946 (2009).
Solomonow, et al., The Ligamento-Muscular Stabilizing System of the Spine, Spine, 23(23):2552-2562 (1998).
Stokes, et al., Surface EMG Electrodes Do Not Accurately Record from Lumbar Multifidus Muscles, Clin. Biomech, 18(1):9-13 (2003) (Abstract Only).
Van Dieen, et al., Trunk Muscle Recruitment Patterns, Spine, 28(8):834-841 (2003) (Abstract Only).
Verrills, et al., Peripheral NErve Stimulation: A Treatment for Chronic Low Back Pain and Failed Back Surgery Syndrome?, Neuromodulation: Technology at the Neural Interface, 12(1):68-75 (2009).

* cited by examiner

APPARATUS AND METHODS FOR ANCHORING ELECTRODE LEADS FOR USE WITH IMPLANTABLE NEUROMUSCULAR ELECTRICAL STIMULATOR

I. CROSS-REFERENCE TO RELATED APPLICATIONS

This application claims the benefit of priority of U.S. Provisional Application Ser. No. 61/514,327, filed Aug. 2, 2011, the entire contents of which are incorporated herein by reference.

II. FIELD OF THE INVENTION

This application generally relates to apparatus and methods for anchoring a medical device, such as an electrical stimulation lead, catheter or other generally elongated or tubular device in the body.

III. BACKGROUND OF THE INVENTION

Many medical devices incorporate an elongated or tubular element that is required to be positioned at a particular anatomical site. Such devices include pacemakers, spinal cord stimulators, peripheral nerve stimulators, and drug delivery catheters.

In the case of a pacemaker, for example, the leads may be threaded through a vein, and then anchored using a fixation element at the distal tip of the lead to prevent dislodgement. Such a fixation element may be a tine, fin, or screw that is secured in the trabeculae of the ventricle.

Generally, it is desirable to implant and anchor a medical device using a minimally invasive approach, and for many devices, a percutaneous approach through a small incision is preferable. One drawback of a percutaneous approach is that relatively large and complex anchoring mechanisms cannot be deployed through the incision or using a needle, catheter, or cannula. Additionally, in many cases, there is no convenient anatomical structure to which the medical device may be anchored.

A spinal cord stimulator (SCS) may include an implantable pulse generator (IPG) connected to one or more leads having one or more electrodes configured to deliver electrical energy to the spinal cord to block pain signals from reaching the brain. Small changes in electrode position may in some cases adversely impact the system's ability to effectively deliver therapy. It may not be practical or feasible to provide an anchoring mechanism inside the spinal canal to anchor a lead of the SCS. The conventional technique for securing the lead is to stabilize the lead using a ligature sleeve or suture sleeve secured to the lead body and attached to the superficial fascia with a suture. This technique, while in common use, suffers from drawbacks including significant incidence of lead dislodgement. Another drawback is that the superficial tissue is often an undesirable distance from the target tissue of stimulation. Any change in patient posture which results in a change in the relative distance between the superficial fascia and the target tissue of stimulation results in tension being applied to the lead body and subsequent movement of the electrodes.

U.S. Patent Application Publication No. 2008/0228241 to Sachs and U.S. Patent Application Publication No. 2011/0224665 to Crosby et al., both assigned to the assignee of the present invention, and both incorporated herein in their entirety by reference, describe implanted electrical stimulation devices that are designed to restore neural drive and rehabilitate the multifidus muscle to improve stability of the spine. Rather than masking pain signals while the patient's spinal stability potentially undergoes further deterioration, the stimulator systems described in those applications are designed to strengthen the muscles that stabilize the spinal column, which in turn is expected to reduce persistent or recurrent pain. Sachs and Crosby also describe peripheral nerve stimulation, in which electrical energy is applied to a nerve to effect a physiological change, such as to elicit a muscle contraction or to block pain signals from traveling in the peripheral nerve.

While the stimulator systems described in the Sachs and Crosby applications seek to rehabilitate the multifidus and restore neural drive, use of those systems necessitates the implantation of one or more electrode leads in the vicinity of a predetermined anatomical site, such as the medial branch of the dorsal ramus nerve to elicit contraction of the lumbar multifidus muscle. For that application, there is no convenient anatomical structure near the distal end of the lead to allow for use of a conventional anchoring mechanism on the lead. Anchoring the lead to the superficial fascia as described above may be effective in many cases, but may still be susceptible to the problems of dislodgement which may prevent proper therapy delivery.

The challenges of anchoring medical devices extend beyond electrical stimulation. For example, an intrathecal pump is a medical device configured to deliver small and metered amounts of a fluid containing a drug to target tissue, such as the spinal cord. The drug may be delivered by a small catheter that is placed inside the spinal canal, and the problems of dislodgement are similar to those described above. It would be desirable to provide a mechanism which more effectively anchors the catheter to prevent dislodgement and the possibility of the drug missing its intended target, or being delivered to an incorrect site.

It would be desirable to provide electrode leads and methods of implantation wherein the lead is securely anchored within a patient, thus reducing the risk of dislodgement of the lead.

It further would be desirable to provide electrode leads and methods of implantation wherein an anchoring mechanism may be deployed using a percutaneous approach, a needle, a catheter, and/or a cannula.

IV. SUMMARY OF THE INVENTION

The present invention overcomes the drawbacks of previously-known systems by providing apparatus and methods for tethering an electrode lead, or other medical device, to an anatomical structure within a patient using a coupling member. The anatomical structure may include a skeletal structure, e.g., bone, a ligament, a tendon, and/or a fascia. At least one anchor configured to be secured to the anatomical structure and at least one electrode lead suitable for neuromuscular stimulation of spinal muscles and/or nerves innervating one or more muscles that contribute to spine stability may be used. The electrode lead may be configured to be coupled to the anchor via the coupling member, e.g., a suture, by securing a first end of the coupling member to the electrode lead and securing a second end of the coupling member to an eyelet of the anchor to place the electrode lead at a desired anatomical site within the patient.

V. BRIEF DESCRIPTION OF THE DRAWINGS

VI. DETAILED DESCRIPTION OF THE INVENTION

The present invention is directed to methods and apparatus for anchoring electrode leads suitable for use with an implantable neuromuscular electrical stimulation ("NMES") device, such as described in the above-incorporated U.S. Patent Application Publication No. US2008/0228241 to Sachs and U.S. Patent Application Publication No. 2011/0224665 to Crosby. The devices described in those applications supply electrical pulses to nerves innervating the spinal muscles, such as the multifidus muscle, and induce contraction of those muscles to effect a therapy designed to restore neural control and rehabilitation of the muscle. The implantable stimulator is disposed subcutaneously, and is coupled to one or more electrode leads having electrodes in contact with the target muscle, or nerves innervating the target muscles, or other anatomical structures associated with the muscle, such as ligaments and tendons. The NMES stimulation supplied by the stimulator applies a pulse regime that is very different than those employed by previously-known Spinal Cord Stimulation therapy devices, where the goal of the stimulation is simply to reduce or block the transmission of pain signals to the patient's brain, rather than rehabilitate the muscle.

While NMES electrode leads may be anchored to an anatomical structure, e.g., a skeletal structure, using a conventional anchoring mechanism disposed on the distal end of a lead for stimulating certain anatomical sites, there are anatomical sites that do not have an anatomical structure conveniently located adjacent thereto for conventional anchoring. Accordingly, the present invention is directed toward anchoring the stimulation leads into an anatomical structure with at least one anchor coupled to at least one coupling member using either minimally invasive or percutaneous techniques. Advantageously, the distance between a stimulation lead and the anchor may be varied using the coupling member to approximate the lead to a desired anatomical site.

Figure 1A:
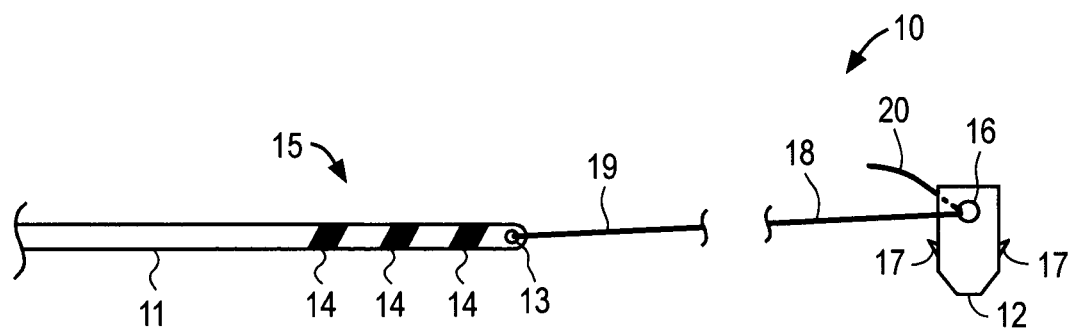
FIGS. 1A and 1B illustrate exemplary kits for tethering an electrode lead to an anatomical structure within a patient using a coupling member.
Figure 1B:
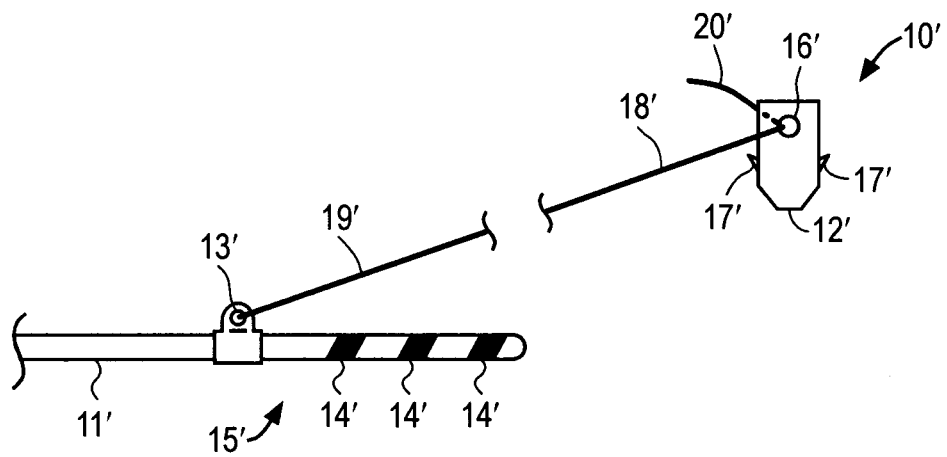

Referring to FIGS. 1A and 1B, exemplary kits 10 and 10' for tethering an electrode lead to an anatomical structure, illustratively a skeletal structure, within a patient using a coupling member are described. In FIGS. 1A and 1B, like elements are described with like-primed numbers. Kit 10 preferably includes lead 11 and anchor 12. Lead 11 may have opening 13 and at least one electrode 14 disposed at distal end 15 of lead 11. Electrodes 14 are configured to deliver electrical energy and may be stimulation electrodes known in the art. Lead 11 illustratively includes three electrodes 14, although the scope of the disclosure is not limited thereto. Anchor 12 may be configured to be anchored to a skeletal structure as is known in the art of orthopedics and may include eyelet 16 and barbs 17. Anchor 12 may comprise a polymer, metal, composite material, ceramic, and/or an allograft and may be coupled to lead 11 using coupling member 18. Coupling member 18 has first and second ends 19 and 20 and may be selected from many types of biocompatible materials well known in the art including a polymer or metal alloy and may braided or monofilament, synthetic or natural, and/or biodegradable. Coupling member 18 may be rigid to maintain a distance between lead 11 and anchor 12, e.g., during tissue compression, or may be flexible such that the distance between lead 11 and anchor 12 may be varied.

First end 19 of coupling member 18 may be coupled to lead 11 at opening 13 as illustrated or may be coupled to lead 11 using a coupling member having a pre-formed knot, a collar that encircles the lead, or a hook that penetrates the lead. Alternatively, the lead may have a section that is comprised of a material that is more compliant than the remainder of the lead body such that coupling member 18 compresses the section when coupling member 18 is tied around the lead. The compression allows coupling member 18 to be securely attached to the lead without increasing the overall outer diameter of the lead body. Coupling member 18 may be flexible.

Second end 20 of coupling member 18 may be coupled to anchor 12 via eyelet 16. Second end 20 may be tied to eyelet 16 or passed through eyelet 16 such that second end 20 may be drawn upon to place lead 11 at a desired anatomical site within the patient.

Referring to FIG. 1B, kit 10' is constructed substantially identically to kit 10 of FIG. 1A, wherein like components are identified by like-primed reference numbers. Thus, for example, lead 11' in FIG. 1B corresponds to lead 11 of FIG. 1A, etc. As will be observed by comparing FIGS. 1A and 1B, first end 19 of coupling member 18 may be coupled to lead 11 at various locations on distal end 15. For example, opening 13 is disposed distal to electrodes 14 and first end 19 of coupling member 18 is coupled to opening 13 in FIG. 1A. However, in FIG. 1B, opening 13' is disposed proximal to electrodes 14' and first end 19' of coupling member 18' is coupled to opening 13'.

Although the kits illustratively include an electrode lead, the kits could readily include an alternative medical device such as a catheter or other generally tubular medical device. Additionally, although the anchor is described as being configured to be anchored to a skeletal structure, the anchor could be readily configured to be anchored to any convenient anatomical structure which provides a stable location, such as a ligament, joint capsule, fibrous membrane, tendon, fascia, and the like.

Figure 2:
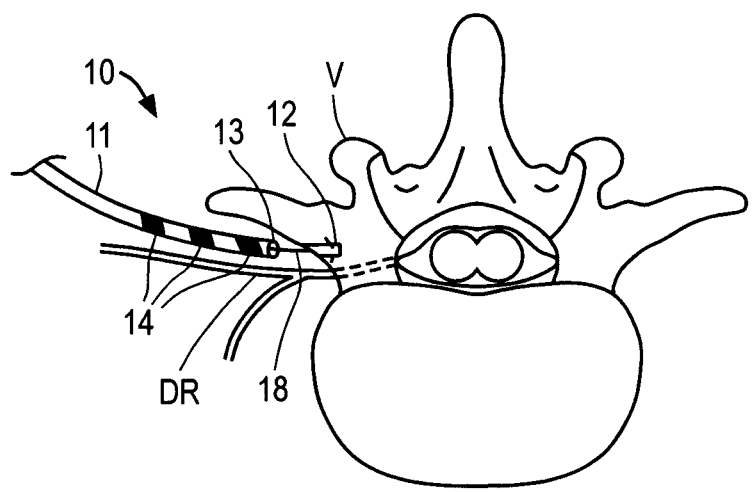
FIG. 2 shows an exemplary method of anchoring an electrode lead suitable for use with a neuromuscular electrical stimulation system.

Referring to FIG. 2, deployment of kit 10 is described. Using fluoroscopic, ultrasonic, anatomic, or CT guidance, a needle, cannula, or catheter is delivered to a skeletal structure, illustratively the transverse process of vertebra V. Using surgical tools and techniques known in the art, a drill is advanced through the needle, cannula, or catheter and a hole is drilled into the skeletal structure. The hole is preferably drilled approximately 2½-3 mm deep into the skeletal structure. Anchor 12 then is delivered to the hole and secured within the hole by barbs 17 or other fixation elements known in the art such as threads, tines, or hooks. Preferably, anchor 12 is delivered having lead 11 coupled thereto by coupling member 18 although lead 11 may be coupled to anchor 12 using coupling member 18 after anchor 12 is secured to the skeletal structure. The length of coupling member 18 may be selected based on the desired placement of electrodes 14 on lead 11. Illustratively, the length of coupling member 18 is determined such that electrodes 14 will be approximated to the medial branch of the dorsal ramus DR nerve when anchor 12 is secured to the transverse process of vertebra V. Advantageously, lead 11 is firmly secured to a skeletal structure and electrodes 14 may be used to stimulate an anatomical site that need not be immediately adjacent to the skeletal structure.

Figure 3A:
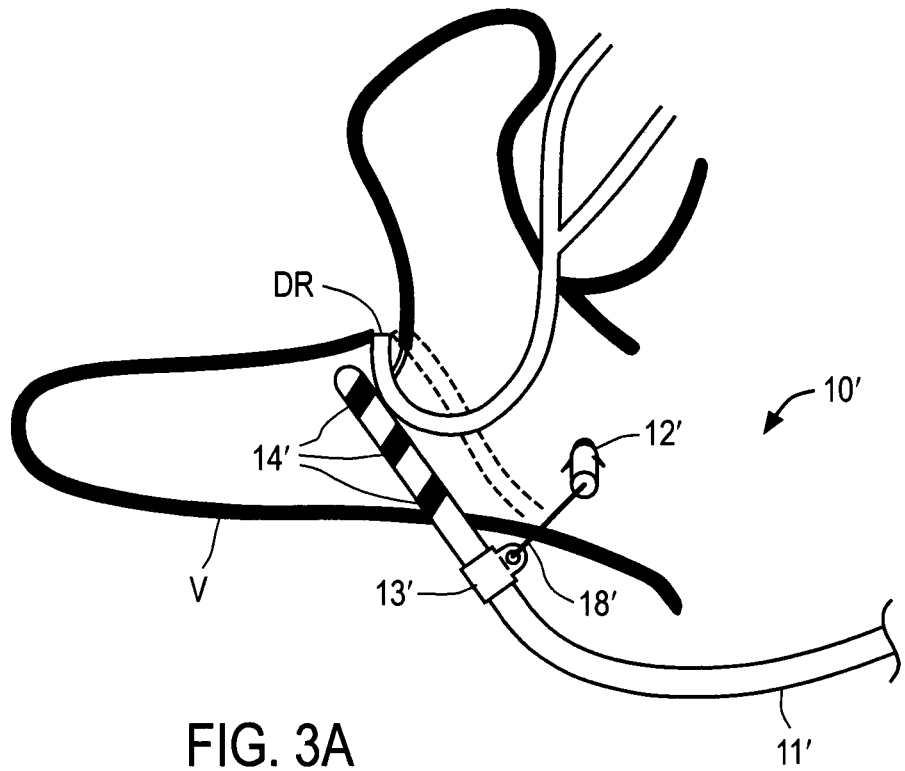
FIG. 3A shows an exemplary method of anchoring an electrode lead coupled to an anchor at an opening proximal to the electrodes on the lead.

Referring now to FIG. 3A, deployment of kit 10' is described. In a manner similar to that described above with respect to FIG. 2, a needle, cannula, or catheter is delivered to a skeletal structure, illustratively the transverse process of vertebra V near the junction with the superior articular process. A drill then is advanced through the needle, cannula, or catheter, a hole is drilled, and anchor 12' is secured within the hole in the skeletal structure. Preferably, anchor 12' is delivered having lead 11' coupled thereto by coupling member 18' although lead 11' may be coupled to anchor 12' using coupling member 18' after anchor 12' is secured to the skeletal structure. The length of coupling member 18' may be selected based on the desired placement of electrodes 14' of lead 11'. Illustratively, the length of coupling member 18' is determined such that electrodes 14' will be approximated to the medial branch of the dorsal ramus DR nerve when anchor 12' is secured to the transverse process of vertebra V. Beneficially, because opening 13' is proximal to electrodes 14' on lead 11', electrodes 14' may be used to stimulate an anatomical site that is distal to the skeletal structure having anchor 12' secured thereto.

Figure 3B:
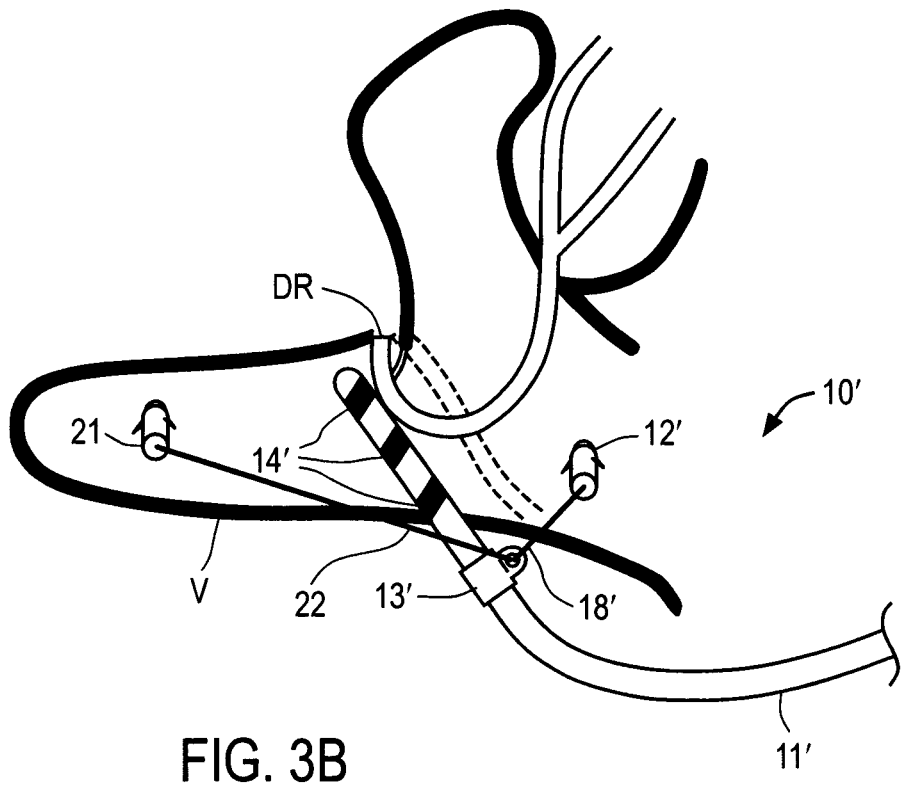
FIG. 3B shows an exemplary method of anchoring the electrode lead of FIG. 3A using a second anchor and a second coupling member.

FIG. 3B depicts an embodiment where kit 10' further includes second anchor 21 and second coupling member 22. Second anchor 21 may be similar to anchor 12 and second coupling member 22 may be similar to coupling member 18 and each may be deployed in similar manners, and thus are not described in detail. In this embodiment, anchor 21 is secured to the vertebra V. Coupling member 22 is coupled to anchor 21 and lead 11' at opening 13', although coupling member 22 may be coupled to lead 11' at a separate opening or another portion of lead 11'. Advantageously, second anchor 21 may be used together with anchor 12' to secure lead 11' at a desired anatomical site.

Anchors 12' and 21 may delivered and secured through the same needle or cannula, or through different needles or cannulas and also may be delivered sequentially. An embodiment for deploying anchors 12' and 21 through the same needle or cannula is now described. Anchor 12' having coupled member 18' attached thereto and anchor 21 having coupling member 22 attached thereto may be loaded within a lumen of the needle or cannula. Anchor 12' then is anchored to an anatomical structure, illustratively a skeletal structure, such that coupling member 18' is retained within the lumen of the needle or cannula. The needle or cannula then is repositioned to an anatomical structure, illustratively a different portion of the skeletal structure, and anchor 21 is anchored to the anatomical structure. Lead 11' then may be inserted into the lumen of the needle or cannula and positioned to the desired anatomical site by adjusting the distance of either or both coupling members 22 and 18'.

Figure 4A:
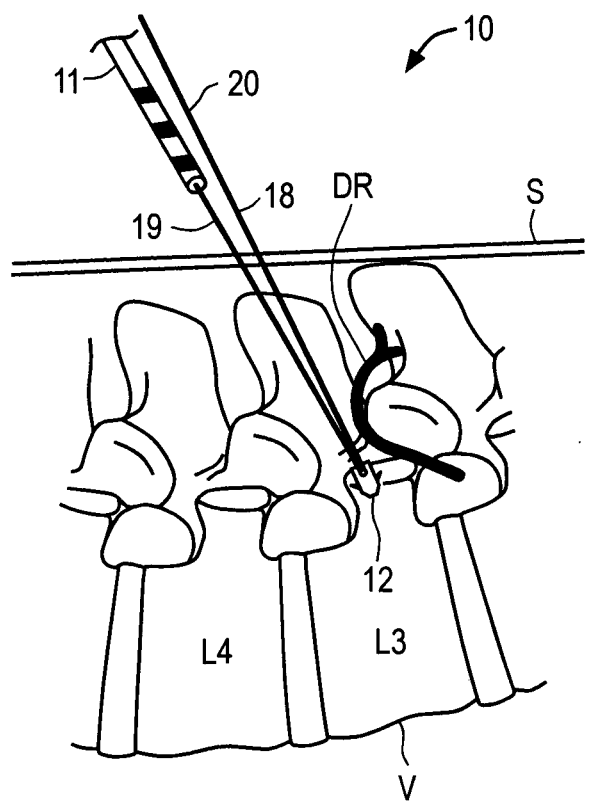
FIGS. 4A and 4B depict an exemplary method of anchoring an electrode lead coupled to an anchor at an opening distal to the electrodes on the lead.
Figure 4B:
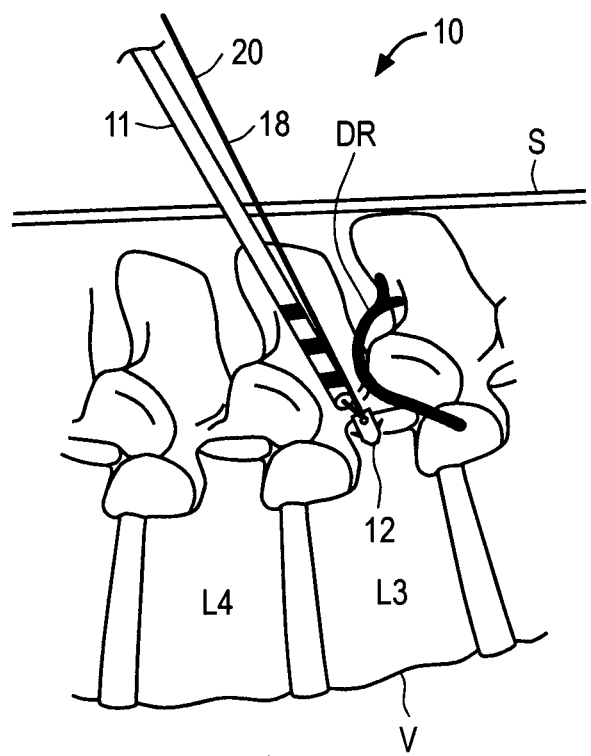

With respect to FIGS. 4A and 4B, an alternative embodiment for deploying kit 10 is described. In a manner similar to that described above with respect to FIGS. 2-3, a needle, cannula, or catheter is delivered to a skeletal structure, illustratively the pedicle of vertebra V. A drill then is advanced through the needle, cannula, or catheter, a hole is drilled, and anchor 12 is secured within the hole in the skeletal structure. Preferably, anchor 12 is delivered having coupling member 18 coupled thereto by passing second end 20 of coupling member 18 through eyelet 16 of anchor 12. Coupling member 18 may be pre-loaded on anchor 12 or may be coupled before delivery. The length of coupling member 18 may be determined such that first and second ends 19 and 20 of coupling member 18 remain outside of the patient's skin S when anchor 12 is secured within the skeletal structure. Lead 11 then may be coupled to first end 19 of coupling member 11 as illustrated in FIG. 4A. Second end 20 of coupling member 18 then may be drawn upon to pass coupling member 18 through eyelet 16 to approximate lead 11 to a desired anatomical site within the patient using, for example, fluoroscopic, acoustic, anatomic or CT guidance. As shown in FIG. 4B, electrodes 14 are illustratively positioned adjacent to the medial branch of the dorsal ramus DR nerve.

Figure 5A:
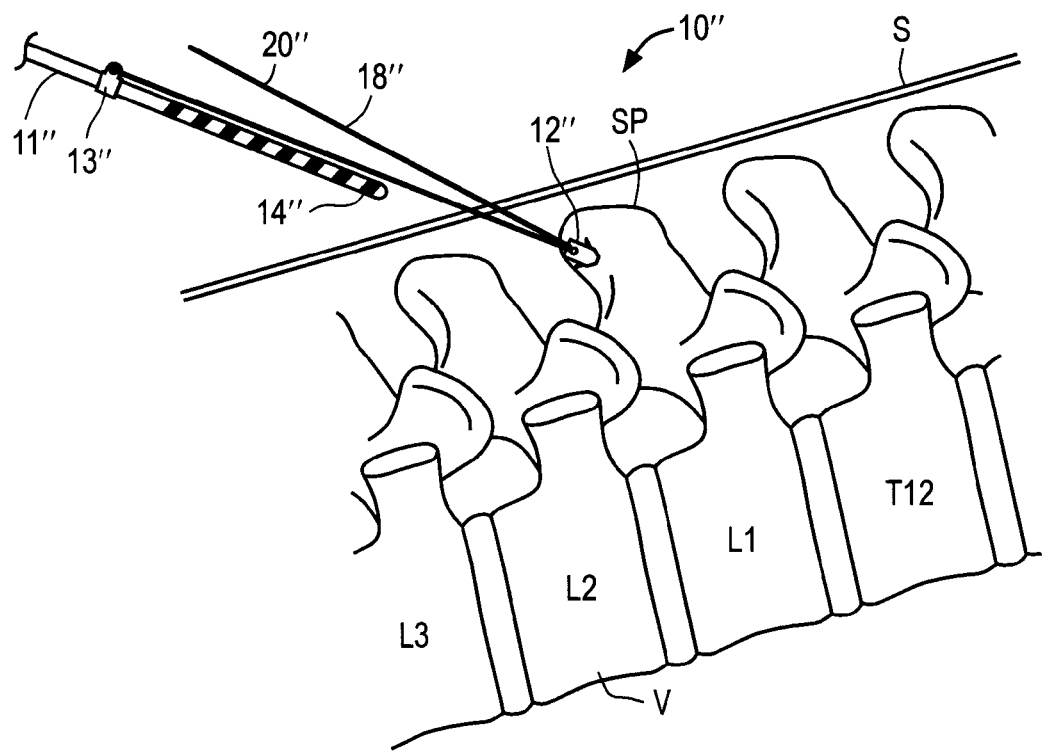
FIGS. 5A and 5B show an alternative method of anchoring an electrode lead coupled to an anchor at an opening proximal to the electrodes on the lead.
Figure 5B:
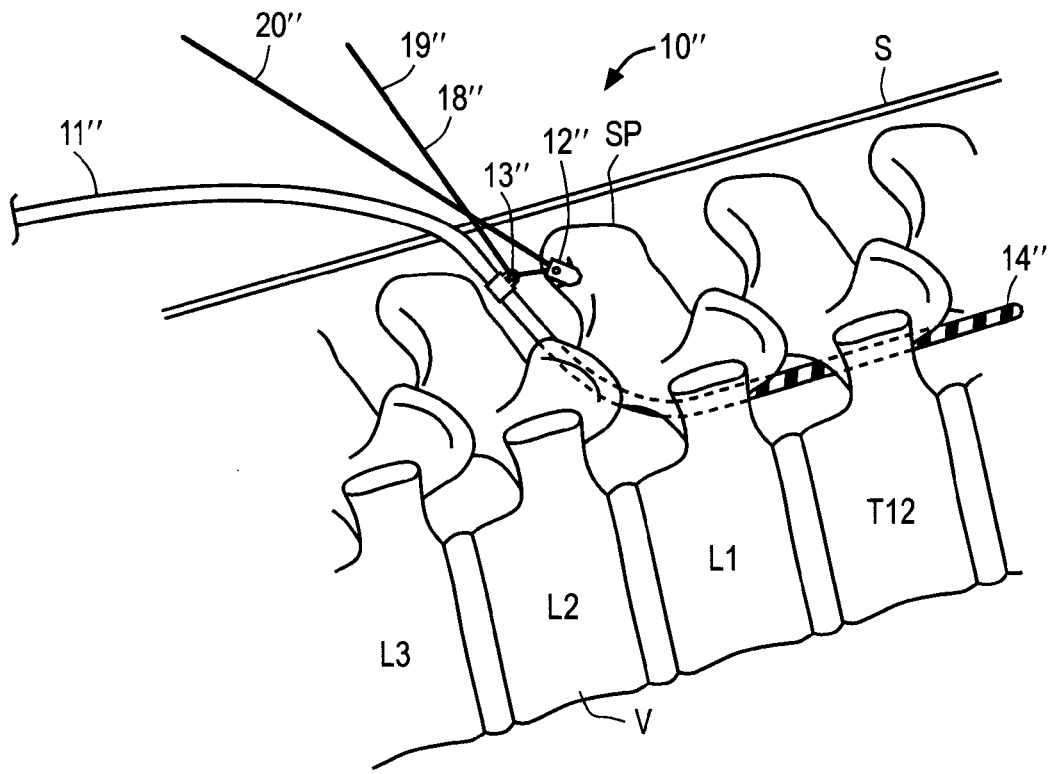

Referring to FIGS. 5A and 5B, deployment of an exemplary kit 10" is described. Kit 10" is constructed substantially identically to kit 10' of FIG. 1B, wherein like components are identified by like-primed reference numbers. As will be observed by comparing FIGS. 5A and 1B, leads 11' and 11" may have various numbers of electrodes 14' and 14". For example, lead 11' illustratively includes three electrodes 14' and lead 11" illustratively includes eight electrodes 14". In a manner similar to that described above with respect to FIGS. 2-4, a needle, cannula, or catheter is delivered to a skeletal structure, illustratively the inferior aspect of the spinous process SP of vertebra V just posterior to the hole through which the epidural space is accessed. A drill then is advanced through the needle, cannula, or catheter, a hole is drilled, and anchor 12" is secured within the hole in the skeletal structure. Preferably, anchor 12" is delivered having coupling member 18" coupled thereto by passing second end 20" of coupling member 18" through eyelet 16" of anchor 12". Coupling member 18" may be pre-loaded on anchor 12" or may be coupled before delivery. The length of coupling member 18" may be determined such that first and second ends 19" and 20" of coupling member 18" remain outside of the patient's skin S when anchor 12" is secured within the skeletal structure. Lead 11" then may be coupled to first end 19" of coupling member 11" as illustrated in FIG. 5A. Second end 20" of coupling member 18" then may be drawn upon to pass coupling member 18" through eyelet 16" to approximate lead 11" to a desired anatomical site within the patient using, for example, fluoroscopic, ultrasonic, anatomic, or CT guidance. A preformed stylet, a steerable stylet, or a guiding catheter may be used to approximate lead 11" to the desired anatomical site. As shown in FIG. 5B, electrodes 14" are illustratively positioned in the epidural space such that electrodes 14" may stimulate a site inside the spinal canal. After lead 11" is advanced to the desired anatomical site, coupling member 18" may be locked in place to prevent further movement of lead 11". Coupling member 18" may be locked in place by tying a knot between first and second ends 19" and 20" of coupling member 18" and advancing the knot to opening 13" of lead 11" using, for example, a knot pushing tool. First and second ends 19" and 20" may then be cut to a suitable length to leave the cut coupling member ends below the patient's skin S.

Figure 6:
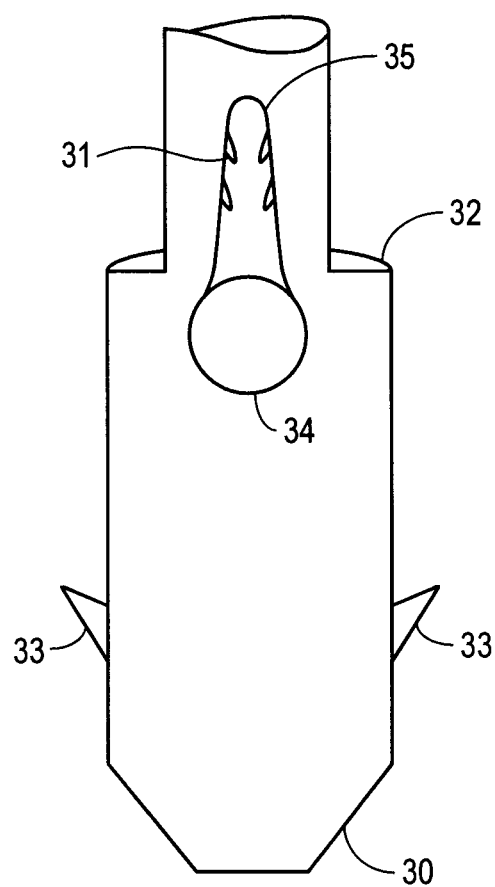
FIG. 6 illustrates an exemplary anchor suitable for use in a kit for tethering an electrode lead to an anatomical structure within a patient using a coupling member.

Referring now to FIG. 6, an anchoring mechanism is described that may be used in kit 10, 10', or 10" in place of anchor 12, 12', 12", or 21. Anchor 30 may be configured to be anchored to a skeletal structure as is known in the art of orthopedics and may include elongated eyelet 31, shoulder 32, and barbs 33 or other fixation elements known in the art such as threads, tines, or hooks. Anchor 30 may comprise a polymer, metal, composite material, ceramic, and/or an allograft. Elongated eyelet 31 is configured to lock the coupling member in place without a knot, and includes large diameter section 34 and small diameter section 35. During deployment of anchor 30, a coupling member may be placed through elongated eyelet 31. A tubular element such as a cannula or catheter may be placed over the proximal diameter of anchor 30 and advanced to shoulder 32 to position the coupling member in larger diameter section 34, allowing for free movement of the coupling member through elongated eyelet 31. A lead may be deployed to a desired anatomical site as described above. Once the lead is positioning at the site, the tubular member is removed. The coupling member may then be drawn upon to cause the coupling member to move into small diameter section 35. The reduced diameter of small diameter section 35 is configured to compress the coupling member and lock it in place. Small diameter section 35 may include a feature such as a thread, roughened surface or protrusions to aid in coupling member retention and prevent the coupling member from sliding back into the large diameter section 34.

Figure 7A:
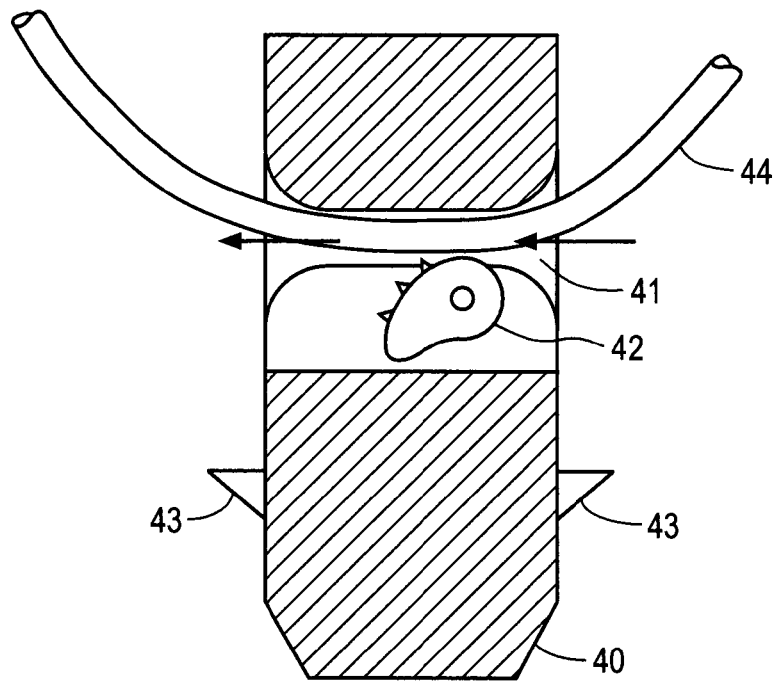
FIGS. 7A and 7B are sectional views of an alternative anchor suitable for use in a kit for tethering an electrode lead to an anatomical structure within a patient using a coupling member.
Figure 7B:
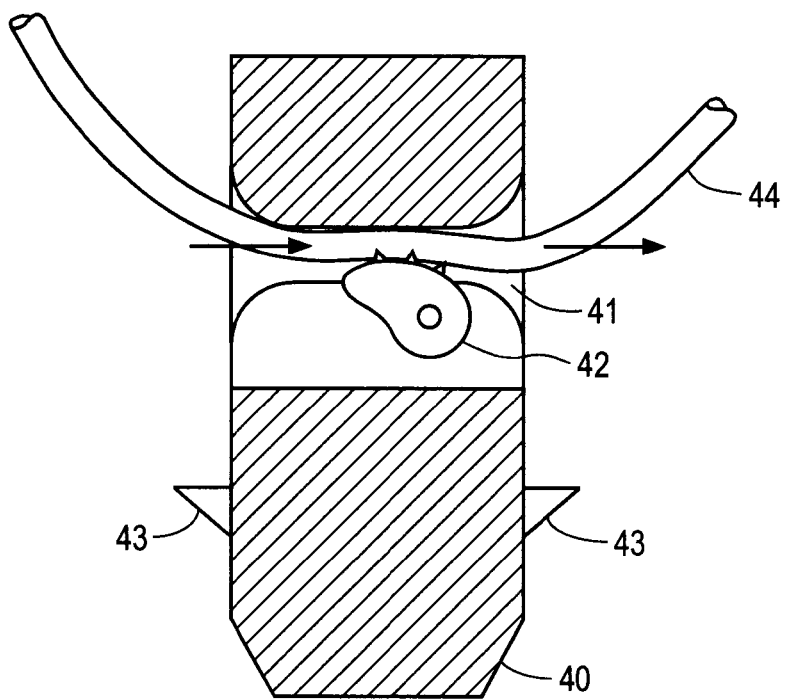

Referring to FIGS. 7A and 7B, an alternative anchoring mechanism is described that may be used in kit 10, 10', or 10" in place of anchor 12, 12', 12", or 21. Anchor 40 may be configured to be anchored to a skeletal structure as is known in the art of orthopedics and may include eyelet 41, locking member 42, and barbs 43 or other fixation elements known in the art such as threads, tines, or hooks. Anchor 40 may comprise a polymer, metal, composite material, ceramic, and/or an allograft. Locking member 42 has an offset diameter and is configured to lock the coupling member in place within eyelet 41 without a knot by allowing coupling member 44 to travel through eyelet 41 in one direction and preventing coupling member 44 from traveling through eyelet 41 in a different direction. During deployment of anchor 40, coupling member 44 may be placed through eyelet 41. As coupling member 44 is advanced as shown in FIG. 7A, locking member 42 retracts and coupling member 44 passes freely through eyelet 41. Coupling member 44 may be advanced, for example, to approximate an electrode lead to a desired anatomical site. As coupling member 44 is moved in a different direction as shown in FIG. 7B, locking member 42 engages and compresses coupling member 44 to prevent relative movement between anchor 40 and coupling member 44, thereby stabilizing the electrode lead location.

Figure 8A:
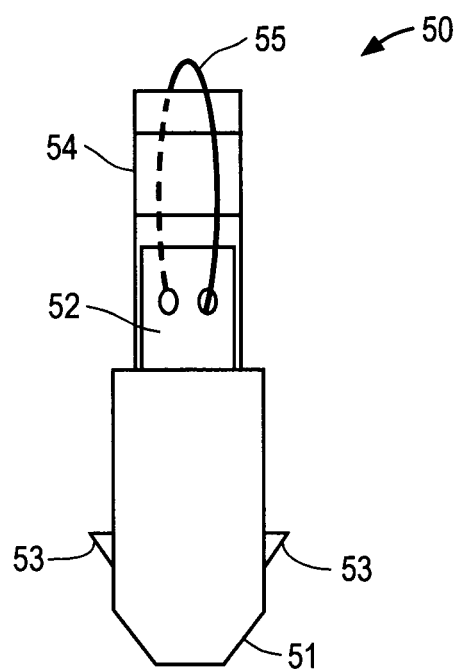
FIG. 8A shows an integrated member suitable for use in a kit for tethering an electrode lead to an anatomical structure within a patient using a coupling member.
Figure 8B:
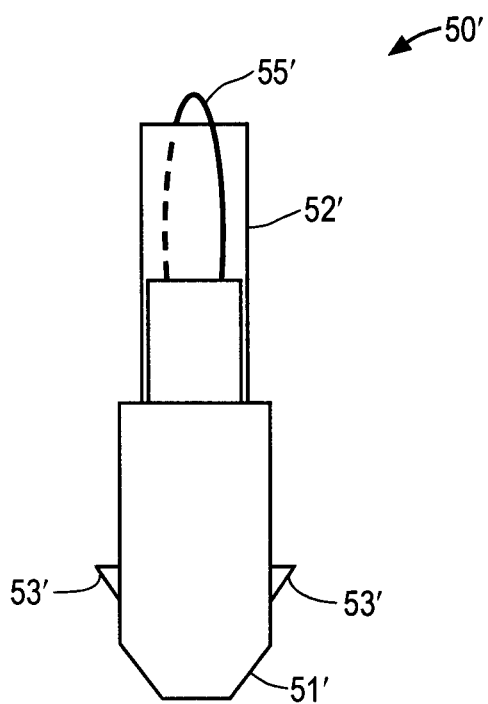
FIG. 8B depicts an alternative integrated member suitable for use in a kit for tethering an electrode lead to an anatomical structure within a patient using a coupling member.

Referring to FIGS. 8A and 8B, integrated members are described that may be used in kit 10, 10', or 10" in place of anchor 12, 12', 12", or 21 and coupling members 18, 18', 18", or 22. Integrated member 50, 50' includes anchor 51, 51' and coupling member 52, 52', respectively. Anchors 51 and 51' may be configured to be anchored to a skeletal structure as is known in the art of orthopedics and may include barbs 53, 53', respectively, or other fixation elements known in the art such as threads, tines, or hooks. Anchors 51 and 51' may comprise a polymer, metal, composite material, ceramic, and/or an allograft.

Coupling member 52 of integrated member 50 shown in FIG. 8A may comprise a polymer such as silicon rubber, metal, composite material, ceramic, and/or an allograft and includes through hole 54 and locking member 55, or other locking member known in the art such as a locking member that may be tightened using crimping or click-locking. Through hole 54 is configured to receive a medical device such as an electrode lead. During deployment of integrated member 50, anchor 51 may be anchored to a skeletal structure, as described above, and an electrode lead may be inserted into through hole 54 using a needle, cannula, and/or guidewire to approximate the electrode lead to a desired anatomical site. The lead then may be locked in place using locking member 55 that illustratively includes a suture that may be tightened to hold the electrode lead in place.

Coupling member 52' of integrated member 50' shown in FIG. 8B may comprise a polymer such as silicon rubber and includes locking member 55', or other locking member known in the art such as a locking member that may be tightened using crimping or click-locking. During deployment of integrated member 50', anchor 51' may be anchored to a skeletal structure, as described above, and an electrode lead may be inserted through a portion of coupling member 52' using a needle or cannula to approximate the electrode lead to a desired anatomical site. The lead then may be locked in place using locking member 55' that illustratively includes a suture that may be tightened to hold the electrode lead in place.

Advantageously, an electrode lead coupled to integrated member 50 or 50' is believed to experience minimal movement relative to the skeletal structure to which the integrated member is anchored.

In an alternative embodiment, integrated member 50, 50' is supplied having the lead pre-attached thereto using coupling member 18, 18', 18", or 22 of FIGS. 1A to 5. In this embodiment, integrated member 50, 50' may be anchored to an anatomical structure as described above and the pre-attached coupling member may be used to approximate the electrode lead to a desired anatomical site as described above with reference to FIGS. 2 to 5.

It should of course be understood that it is within the scope of this invention to provide bilateral stimulation training of the multifidus muscle. It further should be understood that multiple levels, for example the medial branch of the dorsal ramus L3, L4 and L5, may be stimulated by leads to train the multifidus muscle to its fullest extent. While the dorsal ramus nerve is described as the targeted nerve for stimulation, it is within the scope of this patent that stimulation of one or more other anatomical structures such as ligaments, tendons, fascia, and/or nerves of other than spine stabilization muscles (e.g., transverse abdominus, psoas, interspinales, longissimus, ileocostalis, intertransversus, quadratus) may comprise adequate therapy.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:
1. A tethered electrode lead comprising:
a coupling member having a first length; and
a kit comprising an electrode lead having an electrode and a distal end including an opening, and an anchor having an eyelet, the anchor configured to be secured to an anatomical structure,
wherein a first end of the coupling member is coupled to the opening in the electrode lead and a second end of the coupling member is configured to pass through the eyelet of the anchor and the coupling member is adjustable within the patient to a second length, different from the first length, and wherein the coupling member is configured to secure the electrode lead in an implanted position at a desired anatomical site within the patient such that the opening of the electrode lead is spaced apart from the eyelet of the anchor by the second length.

2. The tethered electrode lead of claim 1, wherein the second end of the coupling member is configured to be drawn upon to pass the coupling member through the eyelet to place the electrode lead at the desired anatomical site within the patient.

3. The tethered electrode lead of claim 1, wherein the electrode lead further comprises a collar and the opening is disposed in the collar.

4. The tethered electrode lead of claim 1, wherein the electrode lead further comprises additional electrodes configured to stimulate the desired anatomical site.

5. The tethered electrode lead of claim 1, wherein the opening is disposed on the electrode lead distal to the electrode.

6. The tethered electrode lead of claim 1, wherein the opening is disposed on the electrode lead proximal to the electrode.

7. The tethered electrode lead of claim 1, wherein the second length is selected to place the electrode at a nerve innervating one or more muscles that contribute to spine stability within the patient.

8. The tethered electrode lead of claim 1, wherein the second length is selected to place the electrode at a dorsal ramus nerve within the patient.

9. The tethered electrode lead of claim 1, wherein the anchor further comprises a barbed, threaded, tined, or hooked element, and wherein the anchor is configured to be secured to the anatomical structure using the barbed, threaded, tined, or hooked element.

10. The tethered electrode lead of claim 1, wherein the eyelet of the anchor comprises an elongated eyelet having a large diameter section and a small diameter section, and wherein the small diameter section is configured to lock the coupling member in place when the coupling member enters the small diameter section.

11. The tethered electrode lead of claim 1, wherein the anchor further comprises a locking member disposed adjacent to the eyelet, wherein the locking member is configured to allow the coupling member to travel through the eyelet in one direction and to prevent the coupling member from traveling through the eyelet in a different direction.

* * * * *